US007485463B2

(12) United States Patent
Kawazu et al.

(10) Patent No.: US 7,485,463 B2
(45) Date of Patent: Feb. 3, 2009

(54) NUCLEIC ACIDS ENCODING MIRAFIORI LETTUCE VIRUS PROTEINS AND UTILIZATION THEREOF

(75) Inventors: Yoichi Kawazu, Tsu (JP); Keita Sugiyama, Sapporo (JP); Toshiyuki Morikawa, Toyama (JP); Takahide Sasaya, Tsukuba (JP)

(73) Assignee: National Agricultural and Bio-Oriented Research Organization, Ibaraki (JP)

( * ) Notice: Subject to any disclaimer, the term of this patent is extended or adjusted under 35 U.S.C. 154(b) by 299 days.

(21) Appl. No.: 10/521,596

(22) PCT Filed: Jul. 17, 2003

(86) PCT No.: PCT/JP03/09086

§ 371 (c)(1), (2), (4) Date: Jun. 9, 2005

(87) PCT Pub. No.: WO2004/009817

PCT Pub. Date: Jan. 29, 2004

(65) Prior Publication Data

US 2005/0255457 A1 Nov. 17, 2005

(30) Foreign Application Priority Data

Jul. 18, 2002 (JP) ............................ 2002-209805

(51) Int. Cl.

| | |
|---|---|
| ***C12N 15/82*** | (2006.01) |
| ***C12N 5/10*** | (2006.01) |
| ***C07H 21/04*** | (2006.01) |
| ***A01H 5/00*** | (2006.01) |
| ***C07K 14/00*** | (2006.01) |

(52) U.S. Cl. .................. 435/468; 435/69.7; 435/320.1; 435/419; 530/350; 536/23.72

(58) Field of Classification Search ...................... None
See application file for complete search history.

(56) References Cited

U.S. PATENT DOCUMENTS

| | | | |
|---|---|---|---|
| 5,684,226 | A | 11/1997 | Sarreal |
| 2004/0014032 | A1 | 1/2004 | Sasaya et al. |
| 2007/0264690 | A1 | 11/2007 | Sasaya et al. |

FOREIGN PATENT DOCUMENTS

| | | |
|---|---|---|
| WO | WO 01/90362 | 11/2001 |
| WO | WO 2004/009817 | 1/2004 |

OTHER PUBLICATIONS

Thomas et al., Plant J., 2001, vol. 25, pp. 417-425.*
Klahre et al., PNAS, 2002, vol. 99, pp. 11981-11986.*
New England Biolabs Catalog, 1996/1997, p. 111.*
Baulcombe, D.C., "Mechanisms of Pathogen-Derived Resistance to Viruses in Transgenic Plants," *Plant Cell* 8:1833-1844, American Society of Plant Physiologists (1996).
Kawazu, Y., et al., "Nucleotide sequence of the coat protein gene of Mirafiori lettuce virus," *J. Gen. Plant. Pathol.* 69:55-60, Phytopathological Society of Japan (Feb. 2003).
Mirkov, T.E., and Dobbs, J.A., "Association of Double-Stranded Ribonucleic Acids with Lettuce Big Vein Disease," *Phytopathology* 75:631-635, The American Phytopathological Society (1985).
Roggero, P., et al., "An Ophiovirus isolated from lettuce with big-vein symptoms," *Arch. Virol.* 145:2629-2642, Springer-Verlag (2000).
Sasaya, T., et al., "Amino Acid Sequence of a Protein Encoded in RNA1 of Lettuce Big-vein Virus," presented at The Annual Meeting of the Phytopathological Society of Japan, Abstract No. 2-29, p. 55, Sendai, Japan (Apr. 2-4, 2001).
Sasaya, T., et al., "Nucleotide Sequence of the Coat Protein Gene of Lettuce Big-vein Virus," *Jpn. J. Phytopathol.* 66:298, Abstract No. 64, The Phytopathological Society of Japan (2000).
Sasaya, T., et al., "Nucleotide Sequence of the Coat Protein Gene of Lettuce Big-vein Virus," in the Drafts of Summaries of Speech at the Meeting of the Kansai Division of Phytopathological Society of Japan, p. 74, Abstract No. 64, Kensai, Japan (Oct. 12-13, 2000).
Sasaya, T., et al., "Nucleotide sequence of the coat protein gene of *Lettuce big-vein virus*," *J. Gen. Virol.* 82: 1509-1515, Society for General Microbiology (2001).
van der Wilk, F., et al., "Nucleotide sequence and genomic organization of an ophiovirus associated with lettuce big-vein disease," *J. Gen. Virol.* 83:2869-2877, Cambridge University Press (Nov. 2002).
Vetten, H.J., et al., "Electron Microscopical and Serological Detection of Virus-like Particles Associated with Lettuce Big Vein Disease," *J. Phytopathology* 120:53-59, Paul Parey Scientific Publishers (1987).
Unverified English language translation of WO 01/90362 (Document AL1), 23 pages.
Unverified English language translation of WO 2004/009817 (Document AM1), 17 pages.
Unverified English translation of Document AS2, Sasaya, T., et al., "Amino Acid Sequence of a Protein Encoded in RNA1 of Lettuce Big-vein Virus," presented at The Annual Meeting of the Phytopathological Society of Japan, Abstract No. 2-29, p. 55, Sendai, Japan (Apr. 2-4, 2001).

(Continued)

*Primary Examiner*—Ashwin Mehta
(74) *Attorney, Agent, or Firm*—Sterne, Kessler, Goldstein & Fox, P.L.L.C.

(57) ABSTRACT

The coat protein of Mirafiori lettuce virus was purified from highly purified Mirafiori lettuce virus, and its partial amino acid sequences were determined. DNA encoding the coat protein of Mirafiori lettuce virus was cloned by the polymerase chain reaction using primers designed based on the determined amino acid sequence information, and its primary structure was elucidated. Moreover, the present inventors succeeded in isolating a number of DNA molecules encoding coat protein of Mirafiori lettuce virus by carrying out 5' RACE using primers designed based on the obtained sequence information, and in determining the primary structure. The use of these DNA molecules and their primary structures enables the production of plants resistant to Mirafiori lettuce virus, and the diagnosis of Mirafiori lettuce virus infections.

16 Claims, No Drawings

OTHER PUBLICATIONS

Unverified English translation of Document AT2, Sasaya, T., et al., "Nucleotide Sequence of the Coat Protein Gene of Lettuce Big-vein Virus," *Jpn. J. Phytopathol.* 66:298, Abstract No. 64, The Phytopathological Society of Japan (2000).

Unverified English translation of Document AR3, Sasaya, T., et al., "Nucleotide Sequence of the Coat Protein Gene of Lettuce Big-vein Virus," in the Drafts of Summaries of Speech at the Meeting of the Kansai Division of Phytopathological Society of Japan, p. 74, Abstract No. 64, Kensai, Japan (Oct. 12-13, 2000).

International Search Report for International Patent Application No. PCT/JP01/04268, mailed Aug. 21, 2001, Japanese Patent Office, Tokyo, Japan.

Supplementary European Search Report for European Patent Application No. EP 01 93 2194, mailed Oct. 19, 2004, European Patent Office, Rijswijk, Netherlands.

Clontech Laboratories, Inc., *SMART™ RACE cDNA Amplication Kit, User Manual*, Catalog No. K1811-1, Version No. PR14596, 39 pages, Clontech Laboratories, Inc. (May 2001).

Hull, R., "The Behavior of Salt-Labile Plant Viruses in Gradients of Cesium Sulphate," *Virology* 75:18-25, Academic Press, Inc. (1976).

Navarro, J.A., et al., "Genetic variability in the coat protein genes of lettuce big-vein associated virus and Mirafiori lettuce big-vein virus," *Arch. Virol.* 150:681-694, Springer-Verlag (Dec. 21, 2004).

* cited by examiner

NUCLEIC ACIDS ENCODING MIRAFIORI LETTUCE VIRUS PROTEINS AND UTILIZATION THEREOF

TECHNICAL FIELD

The present invention relates to nucleic acids encoding Mirafiori lettuce viral proteins, proteins encoded by these nucleic acids, and productions and uses thereof.

BACKGROUND ART

Mirafiori lettuce virus (MiLV) was isolated from lettuce showing big-vein symptoms in Italy in 2000 (P. Roggero et al., (2000) Archives of Virology 145: 2629-2642). In 2002, MiLV, rather than Lettuce Big-Vein Virus (LBVV), was reported to be the causative virus of Lettuce big-vein disease (H. Lot et al., (2002) Phytopathology 92: 288-293). MiLV is a soil-borne virus transmitted by the filamentous fungus *Olpidium brassicae*. It has become a problem in the U.S., Japan, and Europe for causing the Lettuce Big-vein disease. The MiLV virus has been reported to be a member of the *Ophiovirus* genus, comprising three genomic minus-strand RNA segments of 8.5 kb, 1.9 kb, and 1.7 kb, and a 48-kDa coat protein as the structural protein. Since this virus has been discovered only recently and its genetic information and such remain unrevealed, no reliable genetic diagnostic methods have been established.

There are several varieties of lettuce that are resistant to MiLV diseases, but their resistance is weak. Furthermore, no useful resistant genetic material has been found. Thus, methods of introducing viral genes into plants will be useful for producing plants with a high-level resistance to this virus. For this purpose, it is necessary to identify the viral gene sequence.

DISCLOSURE OF THE INVENTION

The present invention was achieved in view of the above circumstances. One objective of the present invention is to isolate Mirafiori lettuce viral proteins and nucleic acids encoding them, and to elucidate their nucleic acid structure. Another objective of the present invention is to confer resistance to the Mirafiori lettuce virus by expressing these nucleic acids or their antisense nucleic acids in plants. A further objective of the present invention is to provide methods for diagnosing Mirafiori lettuce virus infection by detecting these nucleic acids or proteins encoded by them.

Mirafiori lettuce virus is an RNA virus, and it is likely that if a DNA encoding a protein of the virus or its antisense DNA is expressed in a plant, the production and function of Mirafiori lettuce viral proteins can be inhibited at the transcription level or translation level (P. F. Tennant, (1994), Phytopathology, 84, 1359-1366; C. C. Huntley & T. C. Hall, (1993), Virology, 192, 290-297; D. C. Baulcombe, (1996), The Plant Cell, 8, 1833-1844).

The present inventors focused on this idea and isolated genes encoding Mirafiori lettuce viral proteins in order to produce plants resistant to the Mirafiori lettuce virus.

Specifically, the present inventors first obtained highly purified Mirafiori lettuce virus, and then applied this to SDS-polyacrylamide gel electrophoresis to detect the coat protein that constitutes this virus. The detected coat protein was purified and then degraded into peptides, followed by determination of their partial amino acid sequences by Edman's methods. Moreover, a DNA encoding the coat protein of Mirafiori lettuce virus was cloned by the polymerase chain reaction, using primers that were designed based on the determined amino acid sequence information, followed by determination of the primary structures.

Next, in order to identify genes that encode full-length coat protein of Mirafiori lettuce virus, RNAs were prepared from the purified virus, and 5' RACE (rapid amplification of cDNA ends) was carried out using these RNA molecules. As a result, the present inventors succeeded in isolating a number of DNA molecules that encode the coat protein of Mirafiori lettuce virus, as well as in determining the primary structure.

The isolated DNA molecules or their antisense molecules are able to confer resistance to Mirafiori lettuce virus through their expression in plants, thereby improving plant productivity. In addition, genetic diagnosis of Mirafiori lettuce virus can be carried out by designing and using primers specific to the Mirafiori lettuce virus, based on the sequence information of isolated DNA molecules. Furthermore, antisera that bind to Mirafiori lettuce virus coat proteins can be produced based on the obtained sequence information, and these can be used for serological diagnosis of Mirafiori lettuce virus.

The present invention was completed based on the above findings. The present invention provides Mirafiori lettuce virus proteins, nucleic acids encoding these proteins, and productions and uses thereof.

More specifically, the present invention provides the following:

[1] A nucleic acid that encodes the coat protein of Mirafiori lettuce virus, comprising (a) or (b) below:

(a) a nucleic acid that encodes a protein comprising the amino acid sequence of SEQ ID NO: 2;

(b) the nucleic acid of (a) that encodes a coding region of the nucleotide sequence of SEQ ID NO: 1;

[2] The nucleic acid of [1], wherein the nucleic acid is an RNA;

[3] The nucleic acid of [1], wherein the nucleic acid is a DNA;

[4] A DNA that encodes a sense RNA complementary to the complementary strand of the nucleic acid of [2];

[5] A DNA that encodes an antisense RNA complementary to the nucleic acid of [2];

[6] A DNA that encodes an RNA having ribozyme activity to specifically cleave the nucleic acid of [2];

[7] A vector that comprises the nucleic acid of [3];

[8] A transformed cell that comprises the nucleic acid of [3] or the vector of [7];

[9] A protein encoded by the nucleic acid of [1];

[10] An antibody that binds to the protein of [9];

[11] A method for producing the protein of [9], wherein said method comprises the steps of:

(a) culturing the transformed cell of [8]; and (b) recovering the expressed protein from said transformed cell or its culture supernatant;

[12] A vector that comprises the DNA of any one of [4] to [6];

[13] A transformed plant cell which carries the nucleic acid of [1], the DNA of any one of [4] to [6], or the vector of [7] or [12];

[14] A transformed plant that comprises the transformed plant cell of [13];

[15] A transformed plant that is a progeny or clone of the transformed plant of [14];

[16] A propagation material of the transformed plant of [14] or [15]; and

[17] A method for diagnosing Mirafiori lettuce virus infection, wherein said method comprises the step of: detecting the nucleic acid of [1] or the protein of [9] in a plant cell or in *Olpidium brassicae,* which is a fungal vector of Mirafiori lettuce virus.

The present invention provides the coat protein of Mirafiori lettuce virus and nucleic acids encoding it. The cDNA nucleotide sequence that encodes the coat protein isolated by the present inventors is shown in SEQ ID NO: 1; and the amino acid sequence of the protein encoded by this cDNA is shown in SEQ ID NO: 2; both of which are included in the present invention. The isolated cDNA consists of a 1,514-bp nucleotide sequence and encodes 437 amino acids. This was the first instant that demonstrated the Mirafiori lettuce virus gene and the primary structure of the encoded protein.

Nucleic acids encoding proteins of the present invention comprise DNAs and RNAs. The DNAs comprise cDNAs and chemically synthesized DNAs. The RNAs comprise viral genomic RNAs, mRNAs, and synthetic RNAs. The nucleic acids of the present invention can be prepared using conventional means by a person with ordinary skill in the art. Specifically, a first-strand DNA can be synthesized by performing a reverse transcription reaction using RNAs prepared from deproteinizing purified virus by SDS-phenol methods and such, or total nucleic acids extracted from a virus-infected leaf by CTAB methods and such, as a template, and using random primers or primers designed based on the sequences of the nucleic acids of the present invention. From the first-strand DNA prepared by this method, a second strand DNA can be synthesized according to the method of Gubler & Hoffman (U. Gubler and B. J. Hoffman, (1983), Gene 25, 263). Then, the DNAs can be cloned into various commercially available plasmids or phagemid vectors. Alternatively, DNAs encoding the RNAs of Mirafiori lettuce virus can be amplified by the polymerase chain reaction, using the first-strand DNA as a template and primers designed based on the nucleic acid sequences of the present invention. The amplified DNAs can be TA cloned using pGEM-T vectors and such, or they can be cloned into various commercially available plasmid vectors by adding restriction enzyme sites to the primers.

The nucleic acids of the present invention can also be used for preparing recombinant proteins and for producing Mirafiori lettuce virus-resistant plants.

In general, when preparing recombinant proteins, a DNA encoding a protein of the present invention is inserted into an appropriate expression vector, the vector construct is introduced into appropriate cells, these transformed cells are cultured, and the expressed protein of interest is purified. For easier purification and such, the recombinant proteins can be expressed as fusion proteins with other proteins. For example, methods that can be applied when *E. coli* is the host (Vector pMAL Series, supplied by New England BioLab, U.S.A.) include preparation as a fusion protein with maltose-binding protein, glutathione S-transferase (GST) (Vector pGEX Series, supplied by Amersham Pharmacia Biotech), or an attached histidine tag (pET Series, supplied by Novagen). The host cells are not particularly limited as long as they are suitable for the expression of recombinant proteins. Host cells such as yeasts, various animal cells, plant cells, and insect cells can be used as well as the above-described *E. coli.* The introduction of vectors into host cells can be carried out by various methods widely known to those skilled in the art. For example, vectors can be introduced into *E. coli* using an introduction method that uses calcium ions (Mandel, M. & Higa, A. (1970) Journal of Molecular Biology, 53, 158-162; Hanahan, D. (1983) Journal of Molecular Biology, 166, 557-580). Recombinant proteins expressed in host cells can be purified and collected from said host cells, or from the supernatant of the culture medium, using methods well known to those skilled in the art. When recombinant proteins are expressed as fusion proteins, such as with the above-described maltose-binding protein, affinity purification can be easily carried out.

The obtained protein can be used to prepare an antibody that binds to the protein. For example, a polyclonal antibody can be prepared by immunizing animals such as rabbits, with a purified protein of the present invention, or a partial peptide thereof, collecting blood after a certain period, and removing blood clots. Monoclonal antibodies can be prepared by fusing myeloma cells to antibody-producing cells from the animals immunized with the above protein or its partial peptide, isolating monoclonal cells producing the target antibody (hybridoma), and generating the antibody from such cells. The obtained antibody can be utilized to purify or detect proteins of the present invention. The antibodies of the present invention comprise antisera, polyclonal antibodies, monoclonal antibodies, and fragments thereof.

Mirafiori lettuce virus-resistant plants can be produced by: introducing a DNA that suppresses the production or function of Mirafiori lettuce viral proteins into plant cells; and regenerating the resulting transformed plant cells.

DNAs encoding RNAs that hybridize with either strand (sense strand or complementary strand thereof) of RNAs encoding Mirafiori lettuce viral proteins can be used as the DNAs that suppress the production and function of Mirafiori lettuce viral proteins.

Examples of the DNAs encoding RNAs that hybridize with viral genomic sense strands and viral mRNAs include DNAs encoding antisense RNAs that are complementary to the transcription products of: a DNA encoding the protein of SEQ ID NO: 2 isolated by the present inventors; and preferably, a DNA comprising a coding region of the nucleotide sequence of SEQ ID NO: 1. Herein, "complementary" is not limited to complete complementarity, as long as the production of Mirafiori lettuce viral proteins can be effectively inhibited. The transcribed RNAs preferably have complementarity of 90% or higher, and more preferably 95% or higher to the RNAs encoding target Mirafiori lettuce viral proteins. Herein, the term "complementarity" refers to the percentage of nucleotides forming complementary nucleotide pairs in the total number of nucleotides in a region, where the two sequences corresponding to each other are aligned to maximize the number of complementary nucleotide pairs.

DNAs encoding sense RNAs complementary to the complementary strand of: an RNA encoding the protein of SEQ ID NO: 2 isolated by the present inventors; and preferably, an RNA comprising a coding region of the nucleotide sequence of SEQ ID NO: 1 can be used as the DNAs that encode RNAs which hybridize with a complementary strand of the viral genomic RNAs. Herein, "complementary" is not limited to complete complementarity as long as the production of Mirafiori lettuce viral proteins can be effectively inhibited. The transcribed sense RNAs preferably have complementarity of 90% or higher, and more preferably 95% or higher to the RNAs (complementary strands) encoding target Mirafiori lettuce viral proteins.

In order to effectively inhibit the expression of a target gene, the above-descried antisense and sense RNAs comprise at least 15 nucleotides or more, more preferably at least 100 nucleotides or more, and still more preferably at least 500 nucleotides or more. These RNAs are generally shorter than 5 kb, and preferably shorter than 2.5 kb.

In addition, it is likely that DNAs encoding a ribozyme that cleaves at least one of the strands of an RNA that encodes Mirafiori lettuce viral proteins can be used as a DNA to suppress the production of the Mirafiori lettuce viral proteins.

"Ribozymes" are RNA molecules with catalytic activities. Ribozymes have various activities, and among them, research on ribozymes that work as RNA cleaving enzymes has enabled the design of ribozymes that site-specifically cleave RNAs. While some ribozymes of the group I intron type or the M1LRNA in RNaseP consist of 400 nucleotides or more, others belonging to the hammerhead type or the hairpin type have an activity domain of about 40 nucleotides (Makoto Koizumi and Eiko Ohtsuka (1990) Tanpakushitsu Kakusan Kohso (Protein, Nucleic acid, and Enzyme) 35: 2191).

The self-cleavage domain of a hammerhead type ribozyme cleaves at the 3' side of C15 of the sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (M. Koizumi et al. (1988) FEBS Lett., 228: 225). If the substrate binding site of the ribozyme is designed to be complementary to the RNA sequences adjacent to the target site, a restriction-enzyme-like RNA cleaving ribozyme which recognizes the sequence UC, UU, or UA within the target RNA can be created (M. Koizumi et al. (1988) FEBS Lett., 239: 285; Makoto Koizumi and Eiko Ohtsuka (1990) Tanpakushitsu Kakusan Kohso (Protein, Nucleic acid, and Enzyme), 35: 2191; M. Koizumi et al. (1989) Nucleic Acids Res., 17: 7059). For example, in a gene of the present invention (SEQ ID NO: 1), multiple sites that can be targeted by the ribozyme are present.

Hairpin-type ribozymes are also useful for the purpose of the present invention. Hairpin-type ribozymes can be found, for example, in the minus strand of the satellite RNAs of Tobacco ringspot virus (J. M. Buzayan, Nature 323: 349 (1986)). This ribozyme has also been shown to target-specifically cleave RNAs (Y. Kikuchi and N. Sasaki (1992) Nucleic Acids Res., 19: 6751; Yo Kikuchi (1992) Kagaku To Seibutsu (Chemistry and Biology) 30: 112).

The ribozyme designed to cleave the target is linked to a promoter such as the cauliflower mosaic virus 35S promoter, and to a transcription termination sequence, so that it will be transcribed in plant cells. However, if extra sequences have been added to the 5' end or 3' end of the transcribed RNA, the ribozyme activity can be lost. In this case, one can place an additional trimming ribozyme, which functions in cis to trim the 5' or 3' side of the ribozyme portion, in order to correctly excise the ribozyme portion from the transcribed RNA comprising the ribozyme (K. Taira et al. (1990) Protein Eng. 3: 733; A. M. Dzianott and J. J. Bujarski (1989) Proc. Natl. Acad. Sci. USA 86: 4823; C. A. Grosshans and R. T. Cech (1991) Nucleic Acids Res., 19: 3875; K. Taira et al. (1991) Nucleic Acid Res., 19: 5125). Multiple sites within the target gene can be cleaved by arranging these structural units in tandem to achieve greater effects (N. Yuyama., (1992) Biochem. Biophys. Res. Commun. 186: 1271). By using such ribozymes, it is possible to specifically cleave the transcription products of a target gene of the present invention to suppress its gene expression.

Vectors to be used in the transformation of plant cells are not limited as long as the vector can express an inserted DNA in the cell. For example, vectors comprising promoters for constitutive gene expression in plant cells (e.g., cauliflower mosaic virus 35S promoter); and inducible promoters that are activated by exogenous stimuli can be used. Examples of preferable vectors include pBI binary vectors. The "plant cells" into which the vector is introduced are not particularly limited; however, plants susceptible to Mirafiori lettuce virus are more preferable considering the objectives of this invention. In addition to lettuce, plants that are susceptible to the Mirafiori lettuce virus comprise, for example, *Chenopodium quinoa* (Chenopodiaceae) and *Nicotiana benthamiana* (Solanaceae) (P. Roggero et al., (2000) Archives of Virology 145: 2629-2642). "Plant cells" can be any type of cells such as suspended culture cells, protoplasts, leaf sections, or calluses, as long as they can be regenerated into a plant.

A vector can be introduced into plant cells by known methods such as the polyethylene glycol methods, polycation methods, electroporation, methods using *Agrobacterium,* and particle bombardment. For example, one of the preferable methods is described in S. Z. Pang et al., (1996), The Plant Journal, 9: 899-909.

A plant can be regenerated from transformed plant cells by methods known to a person with ordinary skill in the art according to the type of plant cell. One example of the preferable regeneration methods is described in S. Enomoto, et al., (1990), Plant Cell Reports, 9: 6-9.

Once a transformed plant in which a DNA of the present invention has been introduced into the genome is obtained, it is possible to obtain progenies from that plant by sexual propagation. Alternatively, plants can be mass-produced from propagation materials (for example, seeds, plantlets, calluses, and protoplasts) obtained from the plant, and progenies or clones thereof. The present invention includes plant cells carrying the DNAs of the present invention; plants comprising these cells; progenies and clones of these plants; and propagation materials of the plants, plant progenies and clones.

In addition, the present invention provides methods for diagnosing Mirafiori lettuce virus infections. One embodiment of the diagnostic methods of the present invention comprises the step of detecting a Mirafiori lettuce viral protein using a primer or probe. Nucleic acid sequences which comprise at least 15 nucleotides that are homologous or complementary to a DNA encoding the Mirafiori lettuce viral protein of SEQ ID NO: 2 can be used as a probe or primer. The nucleic acids are preferably nucleic acids that specifically hybridize to a DNA encoding the Mirafiori lettuce viral protein of SEQ ID NO: 2.

The primers or probes may be labeled as necessary using, for example, radioactive labels.

This diagnostic method, for example, comprises the steps of preparing a test sample from a plant suspected of being infected with the Mirafiori lettuce virus, *Olpidium brassicae* suspected of harboring the virus, or soil containing the virus; and subjecting the sample to polymerase chain reaction (PCR) using the above primers, or Northern blotting analysis using the above probes.

Another embodiment of the diagnostic methods of the present invention is a method comprising the step of detecting Mirafiori lettuce viral proteins using antibodies. Antibodies used in this diagnosis can be prepared by, for example, synthesizing a peptide using the antigenic region deduced from the obtained amino acid sequence (SEQ ID NO: 2), conjugating this peptide to a carrier protein such as KLH or BSA, and immunizing rabbits with the conjugated peptide. In addition, antibodies can be produced by attaching histidine tags to the coat protein of the Mirafiori lettuce virus expressed in *E. coli,* using the QIAexpress Type IV Kit (QIAGEN), and immunizing rabbits with the tagged protein. The antibodies may be labeled as necessary using, for example, enzyme labels. Furthermore, instead of directly labeling the antibodies, the antibodies may also be labeled through substances, such as protein A, that bind to the antibodies for detection of the target protein.

This diagnostic method, for example, comprises the steps of: preparing a test sample from a plant suspected of being infected with the Mirafiori lettuce virus, *Olpidium brassicae* suspected of harboring the virus, or soil containing the virus; and subjecting the sample to ELISA or Western blotting analyses using the above antibodies.

BEST MODE FOR CARRYING OUT THE INVENTION

Herein below, the present invention will be specifically described using Examples, but it is not to be construed as being limited thereto.

EXAMPLE 1

Cloning of Coat-Protein Encoding Genes of Mirafiori Lettuce Virus

Lettuce was seeded into infested soils obtained from lettuce fields in Hyogo Prefecture in 1999. *Chenopodium quinoa* was inoculated with sap from diseased strains, and the already multiplied virus was further grown in *C. quinoa* to be used as materials for producing purified virus. Virus purification was carried out by modifying the purification method for the Tulip mild mottle mosaic virus used by Morikawa et al. (T. Morikawa et al., (1995), Ann. Phytopathol. Soc. Jpn. 61: 578-581). First, Mirafiori lettuce virus-infected leaves were homogenized with Tris-HCl (pH8.0) comprising 5 mM Na-DIECA, 0.1% (v/v) 2-mercaptoethanol, and 1 mM Na-EDTA. Treatment with carbon tetrachloride was omitted. Instead of the final CsCl density gradient centrifugation, $Cs_2SO_4$ density gradient centrifugation was carried out to obtain a virus fraction. The purified virus fraction obtained by this purification method was subjected to electrophoresis on SDS-polyacrylamide gel, and a single 48-kDa band was detected. Furthermore, electron microscopy revealed only the MiLV particles and no contaminants, indicating that the purified virus sample is highly pure.

Viral nucleic acids were obtained by phenol/chloroform extraction of the purified virus followed by ethanol precipitation. First-strand cDNA was prepared using $p(dN)_6$ primers and the First-strand cDNA Synthesis Kit (Amersham Pharmacia Biotech).

The internal amino acid sequence of a MiLV coat protein was determined by the following peptide mapping method. The purified MiLV was subjected to electrophoresis on a 10% polyacrylamide gel, and stained using Coomassie Brilliant Blue. A target 48-kDa band was excised from the stained gel, followed by carboxymethylation and lysylendopeptidase treatment. After the treatment, 81 band patterns were obtained by peptide mapping using reverse-phase HPLC. The amino acid sequences of several of these patterns were determined.

Two primers, dYK5 (GARGGIGARACIGCIAT/SEQ ID NO: 5) and dYK8 (SWIACYTCIGTIGGIAR/SEQ ID NO: 6), were designed based on the EGETAI (SEQ ID NO: 3) and LPTEVS (SEQ ID NO: 4) sequences from the obtained amino acid sequences. A PCR product of approximately 750-bp was obtained by PCR using these primers and a Taq DNA Polymerase (Promega). The PCR product was cloned using the PGEM-T Easy Vector System (Promega) and a portion of the nucleotide sequence encoding the coat protein was determined.

Since the purified MiLV virus comprises both plus and minus strand RNAs, the entire nucleotide sequence of the coat protein gene can be determined by 5' RACE alone. The first-strand cDNA to be used in the RACE method was synthesized using $p(dN)_6$ primers and the SMART RACE cDNA Amplification Kit (CLONTECH). Next, primers specific to the nucleotide sequence encoding the coat protein gene were used in the RACE method, and PCR products of approximately 750 bp and 700 bp were obtained. The PCR products were cloned using the pGEM-T Easy Vector System (Promega) and their nucleotide sequences were determined.

The 1514-bp nucleotide sequence represented by SEQ ID NO: 1 was determined by the above method. Translation starts at nucleotide position 86 of this sequence, encoding the 437 amino acids set forth in SEQ ID NO: 2.

INDUSTRIAL APPLICABILITY

In the present invention, the nucleotide sequences of MiLV coat protein genes and their adjacent genes were determined in order to generate transgenic plants. This sequence information can be used to develop MiLV-resistant transgenic plants by introducing a MiLV coat protein gene and its adjacent genes, or antisense genes thereof. Based on this sequence information, MiLV specific primers can also be designed for MiLV genetic diagnoses. Furthermore, antisera can be produced against the peptides synthesized based on the amino acid sequences of the obtained MiLV coat protein, or MiLV coat proteins expressed by *E. coli* for serological diagnoses.

The invention claimed is:

1. An isolated nucleic acid that encodes the coat protein of Mirafiori lettuce virus, comprising (a) or (b) below:

(a) a nucleic acid that encodes a protein comprising the amino acid sequence of SEQ ID NO: 2;

(b) the nucleic acid of (a) that comprises a coding region of the nucleotide sequence of SEQ ID NO: 1.

2. The isolated nucleic acid of claim 1, wherein the nucleic acid is an RNA.

3. The isolated nucleic acid of claim 1, wherein the nucleic acid is a DNA.

4. A vector that comprises the nucleic acid of claim 3.

5. A transformed cell comprising the nucleic acid according to claim 3.

6. An isolated Mirafiori lettuce virus coat protein having the amino acid sequence set forth in SEQ ID NO: 2.

7. A method for producing the protein according to claim 6, wherein said method comprises the steps of:

(a) culturing a transformed cell comprising a nucleic acid that encodes the coat protein of Mirafiori lettuce virus, comprising:

(i) a nucleic acid that encodes a protein comprising the amino acid sequence of SEQ ID NO: 2, or (ii) the nucleic acid of (i) that comprises a coding region of the nucleotide sequence of SEQ ID NO: 1, or a vector comprising the nucleic acid of (i) or (ii); and (b) recovering the expressed protein from said transformed cell or its culture supernatant.

8. A transformed cell comprising the vector according to claim 4.

9. A transformed plant cell which carries the nucleic acid according to claim 1, or the vector according to 4.

10. A transformed plant that comprises the transformed plant cell of claim 9.

11. A transformed plant that is a progeny or clone of the transformed plant of claim 10, wherein the progeny comprises (i) a nucleic acid that encodes a protein comprising the amino acid sequence of SEQ ID NO: 2, or (ii) the nucleic acid of (i) that comprises a coding region of the nucleotide sequence of SEQ ID NO: 1, or a vector comprising the nucleic acid of (i) or (ii).

12. A propagation material of the transformed plant according to claim 10, wherein said material comprises the nucleic acid of claim 1, or the vector of claim 4.

13. An isolated DNA that encodes a sense RNA comprising at least 100 nucleotides that is 100% complementary to, and hybridizes with, a nucleic acid that is 100% complementary to an RNA that encodes the coat protein of Mirafiori lettuce virus, comprising (a) or (b) below:

(a) a nucleic acid that encodes a protein comprising the amino acid sequence of SEQ ID NO: 2;

(b) the nucleic acid of (a) that encodes a coding region of the nucleotide sequence Of SEQ ID NO: 1.

14. An isolated DNA that encodes an antisense RNA comprising at least 100 nucleotides that is 100% complementary to, and hybridizes with, an RNA that encodes the coat protein of Mirafiori lettuce virus, comprising (a) or (b) below:

(a) a nucleic acid that encodes a protein comprising the amino acid sequence of SEQ ID NO: 2;

(b) the nucleic acid of (a) that encodes a coding region of the nucleotide sequence Of SEQ ID NO: 1.

15. An isolated DNA that encodes a sense RNA comprising at least 100 nucleotides that is 100% complementary to a nucleic acid that is 100% complementary to bases 87-1400 of the nucleic acid sequence of SEQ ID NO: 1.

16. An isolated DNA that encodes an antisense RNA comprising at least 100 nucleotides that is 100% complementary to bases 87-1400 of the nucleic acid sequence of SEQ ID NO: 1.

* * * * *

SEQUENCE LISTING

```
<160> NUMBER OF SEQ ID NOS: 6

<210> SEQ ID NO 1
<211> LENGTH: 1514
<212> TYPE: DNA
<213> ORGANISM: mirafiori lettuce virus
<220> FEATURE:
<221> NAME/KEY: CDS
<222> LOCATION: (87)..(1400)

<400> SEQUENCE: 1

gattattttt taaaaatata acaagctcat aagaaaacaa cttctccact caaaagtgaa      60

tcttttcaaa gaaaaacaaa gtcaca atg tca gga gta tac aag gtt tcc gga      113
                             Met Ser Gly Val Tyr Lys Val Ser Gly
```

-continued 1 5 att cag tct atc ttg caa aaa gat gtg act tcc gaa gga gaa aca gct 161
Ile Gln Ser Ile Leu Gln Lys Asp Val Thr Ser Glu Gly Glu Thr Ala
10 15 20 25 att cta att tct ctt ggt ctc atg aca aaa gaa gag aag cct gtt cct 209
Ile Leu Ile Ser Leu Gly Leu Met Thr Lys Glu Glu Lys Pro Val Pro
30 35 40 gca aaa atg gcc atg gtg gca tct gca aaa gca aac tca atc atc ttt 257
Ala Lys Met Ala Met Val Ala Ser Ala Lys Ala Asn Ser Ile Ile Phe
45 50 55 gtt tcg gaa gat ggc tct ttg tct ttt gaa gct cca aaa gaa aca gga 305
Val Ser Glu Asp Gly Ser Leu Ser Phe Glu Ala Pro Lys Glu Thr Gly
60 65 70 gag acc agc aaa cca gga gag aag aaa gag gaa aag aag gta gaa gtg 353
Glu Thr Ser Lys Pro Gly Glu Lys Lys Glu Glu Lys Lys Val Glu Val
75 80 85 gga gtc aag ttt cct ttc agc gca gcc aaa gta aag gag cta att gaa 401
Gly Val Lys Phe Pro Phe Ser Ala Ala Lys Val Lys Glu Leu Ile Glu
90 95 100 105 ggg aaa agt ctt act ttg gat cag gac aaa atc caa aaa gtg ctg gaa 449
Gly Lys Ser Leu Thr Leu Asp Gln Asp Lys Ile Gln Lys Val Leu Glu
110 115 120 gaa tat gtt aag aat ttg cca agg act gct gag act tac aaa cca aaa 497
Glu Tyr Val Lys Asn Leu Pro Arg Thr Ala Glu Thr Tyr Lys Pro Lys
125 130 135 gag att gag atc aaa tgt ttc aag ggt gtt gac ttc agt ata agc agt 545
Glu Ile Glu Ile Lys Cys Phe Lys Gly Val Asp Phe Ser Ile Ser Ser
140 145 150 ttg ctt tct tca ggg acc aaa atc tta gat gct att ctt tac agt act 593
Leu Leu Ser Ser Gly Thr Lys Ile Leu Asp Ala Ile Leu Tyr Ser Thr
155 160 165 tac aag gat tca gca gag cac aac ttc ata ttt gat gtg aaa gtt cta 641
Tyr Lys Asp Ser Ala Glu His Asn Phe Ile Phe Asp Val Lys Val Leu
170 175 180 185 tct cct gat ttc atc gat agc aag tta ctc gtg aac aac atc gaa aca 689
Ser Pro Asp Phe Ile Asp Ser Lys Leu Leu Val Asn Asn Ile Glu Thr
190 195 200 ggc aat cga gca atc aaa gca gct ttc tgt ctt gtt tac aat caa ggt 737
Gly Asn Arg Ala Ile Lys Ala Ala Phe Cys Leu Val Tyr Asn Gln Gly
205 210 215 gga ttg cca tca aag acg agt gaa gaa cga cca cta tct aag ttt gta 785
Gly Leu Pro Ser Lys Thr Ser Glu Glu Arg Pro Leu Ser Lys Phe Val
220 225 230 aga gaa acg ata ttc cgt gag aaa gat ctc aaa gct aac gag tta tgt 833
Arg Glu Thr Ile Phe Arg Glu Lys Asp Leu Lys Ala Asn Glu Leu Cys
235 240 245 gaa tat ctg tca tca gca gat cct tct ttg ttt cca agt caa gtc ttt 881
Glu Tyr Leu Ser Ser Ala Asp Pro Ser Leu Phe Pro Ser Gln Val Phe
250 255 260 265 ttg aaa atc tca ctt gaa aac ctt cct act gag gtt tca tca cgt tgc 929
Leu Lys Ile Ser Leu Glu Asn Leu Pro Thr Glu Val Ser Ser Arg Cys
270 275 280 aag atg tcg att gcg ggc aac aaa gca atg aga tat gca ctc tta gct 977
Lys Met Ser Ile Ala Gly Asn Lys Ala Met Arg Tyr Ala Leu Leu Ala
285 290 295 caa aag ttt gac aaa gat gaa att cca gtt cca aca gaa gtg aat cct 1025
Gln Lys Phe Asp Lys Asp Glu Ile Pro Val Pro Thr Glu Val Asn Pro
300 305 310 aca act agc tca gaa tac atg cag aaa aag gag aaa ata gaa aaa gca 1073

-continued

```
Thr Thr Ser Ser Glu Tyr Met Gln Lys Lys Glu Lys Ile Glu Lys Ala
    315                 320                 325

aaa aag ata gtt gat gtt cta tgt tct ctt gct tct gac ttc cag gca     1121
Lys Lys Ile Val Asp Val Leu Cys Ser Leu Ala Ser Asp Phe Gln Ala
330                 335                 340                 345

caa gtg aaa atg cat cct ctc tcc cct gag aga tca tcg agg aag aat     1169
Gln Val Lys Met His Pro Leu Ser Pro Glu Arg Ser Ser Arg Lys Asn
                350                 355                 360

ttc act ctg caa ttg act tct gca att gtt act tca ctt tcc tac aaa     1217
Phe Thr Leu Gln Leu Thr Ser Ala Ile Val Thr Ser Leu Ser Tyr Lys
            365                 370                 375

ggg agg tta gac atg aga aaa gca atc gaa gag aaa aag ata gag gct     1265
Gly Arg Leu Asp Met Arg Lys Ala Ile Glu Glu Lys Lys Ile Glu Ala
        380                 385                 390

ttc aaa aga gat gaa aat ata ttt gga agg tta aat gct ctt gga caa     1313
Phe Lys Arg Asp Glu Asn Ile Phe Gly Arg Leu Asn Ala Leu Gly Gln
    395                 400                 405

ccc acg ttt cct gtt ctg act aac gca gat gct gac ttt tct gaa ttg     1361
Pro Thr Phe Pro Val Leu Thr Asn Ala Asp Ala Asp Phe Ser Glu Leu
410                 415                 420                 425

tca gtt gag gcc gtg aag aca gct tac gga aag aaa tga gggcagaatc      1410
Ser Val Glu Ala Val Lys Thr Ala Tyr Gly Lys Lys
                430                 435

ggagtgaata gtgaagaatg tggaattgtg gacagatttg ctttttttccg cttatccttt   1470

gcgataggga gtatgtgaac tgatagtttt aataaaaaac tatc                    1514


<210> SEQ ID NO 2
<211> LENGTH: 437
<212> TYPE: PRT
<213> ORGANISM: mirafiori lettuce virus

<400> SEQUENCE: 2

Met Ser Gly Val Tyr Lys Val Ser Gly Ile Gln Ser Ile Leu Gln Lys
  1               5                  10                  15

Asp Val Thr Ser Glu Gly Glu Thr Ala Ile Leu Ile Ser Leu Gly Leu
             20                  25                  30

Met Thr Lys Glu Glu Lys Pro Val Pro Ala Lys Met Ala Met Val Ala
         35                  40                  45

Ser Ala Lys Ala Asn Ser Ile Ile Phe Val Ser Glu Asp Gly Ser Leu
     50                  55                  60

Ser Phe Glu Ala Pro Lys Glu Thr Gly Glu Thr Ser Lys Pro Gly Glu
 65                  70                  75                  80

Lys Lys Glu Glu Lys Lys Val Glu Val Gly Val Lys Phe Pro Phe Ser
                 85                  90                  95

Ala Ala Lys Val Lys Glu Leu Ile Glu Gly Lys Ser Leu Thr Leu Asp
            100                 105                 110

Gln Asp Lys Ile Gln Lys Val Leu Glu Glu Tyr Val Lys Asn Leu Pro
        115                 120                 125

Arg Thr Ala Glu Thr Tyr Lys Pro Lys Glu Ile Glu Ile Lys Cys Phe
    130                 135                 140

Lys Gly Val Asp Phe Ser Ile Ser Ser Leu Leu Ser Ser Gly Thr Lys
145                 150                 155                 160

Ile Leu Asp Ala Ile Leu Tyr Ser Thr Tyr Lys Asp Ser Ala Glu His
                165                 170                 175

Asn Phe Ile Phe Asp Val Lys Val Leu Ser Pro Asp Phe Ile Asp Ser
            180                 185                 190
```

-continued

```
Lys Leu Leu Val Asn Asn Ile Glu Thr Gly Asn Arg Ala Ile Lys Ala
        195                 200                 205

Ala Phe Cys Leu Val Tyr Asn Gln Gly Gly Leu Pro Ser Lys Thr Ser
    210                 215                 220

Glu Glu Arg Pro Leu Ser Lys Phe Val Arg Glu Thr Ile Phe Arg Glu
225                 230                 235                 240

Lys Asp Leu Lys Ala Asn Glu Leu Cys Glu Tyr Leu Ser Ser Ala Asp
                245                 250                 255

Pro Ser Leu Phe Pro Ser Gln Val Phe Leu Lys Ile Ser Leu Glu Asn
            260                 265                 270

Leu Pro Thr Glu Val Ser Ser Arg Cys Lys Met Ser Ile Ala Gly Asn
        275                 280                 285

Lys Ala Met Arg Tyr Ala Leu Leu Ala Gln Lys Phe Asp Lys Asp Glu
    290                 295                 300

Ile Pro Val Pro Thr Glu Val Asn Pro Thr Thr Ser Ser Glu Tyr Met
305                 310                 315                 320

Gln Lys Lys Glu Lys Ile Glu Lys Ala Lys Lys Ile Val Asp Val Leu
                325                 330                 335

Cys Ser Leu Ala Ser Asp Phe Gln Ala Gln Val Lys Met His Pro Leu
            340                 345                 350

Ser Pro Glu Arg Ser Ser Arg Lys Asn Phe Thr Leu Gln Leu Thr Ser
        355                 360                 365

Ala Ile Val Thr Ser Leu Ser Tyr Lys Gly Arg Leu Asp Met Arg Lys
    370                 375                 380

Ala Ile Glu Glu Lys Lys Ile Glu Ala Phe Lys Arg Asp Glu Asn Ile
385                 390                 395                 400

Phe Gly Arg Leu Asn Ala Leu Gly Gln Pro Thr Phe Pro Val Leu Thr
                405                 410                 415

Asn Ala Asp Ala Asp Phe Ser Glu Leu Ser Val Glu Ala Val Lys Thr
            420                 425                 430

Ala Tyr Gly Lys Lys
        435


<210> SEQ ID NO 3
<211> LENGTH: 6
<212> TYPE: PRT
<213> ORGANISM: mirafiori lettuce virus

<400> SEQUENCE: 3

Glu Gly Glu Thr Ala Ile
  1               5


<210> SEQ ID NO 4
<211> LENGTH: 6
<212> TYPE: PRT
<213> ORGANISM: mirafiori lettuce virus

<400> SEQUENCE: 4

Leu Pro Thr Glu Val Ser
  1               5


<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: an
      artificially synthesized primer sequence
<220> FEATURE:
```

-continued

```
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 5

garggngara cngcnat                                                17


<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: an
      artificially synthesized primer sequence
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (15)
<223> OTHER INFORMATION: i

<400> SEQUENCE: 6

swnacytcng tnggnar                                                17
```